United States Patent
Mordarski et al.

Patent Number: 5,843,406
Date of Patent: Dec. 1, 1998

[54] DUAL COMPONENTS ANTIPLAQUE DENTIFRICE COMPOSITIONS

[75] Inventors: Theresa D. Mordarski, Brunswick; Abdul Gaffar, Princeton, both of N.J.

[73] Assignee: Colgate Palmolive Company, New York, N.Y.

[21] Appl. No.: 6,011

[22] Filed: Jan. 12, 1998

[51] Int. Cl.$^6$ .................... A61K 7/16; A61K 7/18
[52] U.S. Cl. .................... 424/49; 424/52; 424/57
[58] Field of Search .................... 424/49–88

[56] References Cited

U.S. PATENT DOCUMENTS

| | | | |
|---|---|---|---|
| 4,980,153 | 12/1990 | Jackson et al. | 424/52 |
| 5,145,667 | 9/1992 | Ibrahim et al. | 424/52 |
| 5,296,214 | 3/1994 | Gaffar . | |
| 5,424,059 | 6/1995 | Prencipe et al. | 424/52 |
| 5,578,295 | 11/1996 | Francis et al. | 424/57 |
| 5,599,525 | 2/1997 | Hsu, I et al. | 424/49 |
| 5,648,064 | 7/1997 | Gaffar et al. | 424/49 |
| 5,690,913 | 11/1997 | Hsu, II et al. | 424/49 |
| 5,693,314 | 12/1997 | Campbell et al. | 424/52 |

FOREIGN PATENT DOCUMENTS

| | | |
|---|---|---|
| 397452A2 | 11/1990 | European Pat. Off. . |
| 691 124A1 | 1/1996 | European Pat. Off. . |
| 799568A1 | 10/1997 | European Pat. Off. . |
| 03005416 A2 | 1/1991 | Japan . |
| 9301837 A | 5/1995 | Netherlands . |
| 96 09034A1 | 3/1996 | WIPO . |
| 96 29047A1 | 9/1996 | WIPO . |

OTHER PUBLICATIONS

Tahmassebl et al Caries Res. 28(4):272–276 Effect of a Calcium Carbonate–Based Toothpaste With 0.3% Triclofan on pH Changes in Dental Plaque in vivo, 1994.

*Primary Examiner*—Shep K. Rose
*Attorney, Agent, or Firm*—Paul Shapiro

[57] ABSTRACT

A dual component antiplaque dentifrice composition in which the first component is an extrudible dentifrice composition containing a nonionic antibacterial agent in which calcium salts are absent and the second component is an extrudable dentifrice composition containing a calcium salt wherein maximum antibacterial agent uptake by dental tissue is achieved when the components and are physically separated prior to use and are mixed upon application to dental tissue.

16 Claims, No Drawings

DUAL COMPONENTS ANTIPLAQUE DENTIFRICE COMPOSITIONS

BACKGROUND OF THE INVENTION

1. Field of the Invention

The present invention relates to a dual component oral care composition which is effective in the retardation and prevention of bacterial plaque accumulation on the teeth.

2. The Prior Art

Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of nonionic antibacterial agents have been suggested in the art to retard plaque formation and the oral infections and dental disease associated with plaque formation. For example, halogenated hydroxydiphenyl ether compounds such as Triclosan are well known to the art for their antibacterial activity and have been used in oral compositions to counter plaque formation by bacterial accumulation in the oral cavity.

The effectiveness of antibacterial agents in retarding plaque formation is dependent upon the amount of the agent which is available for deposition on the dental tissue being treated. It is, therefore, desirable to formulate dentifrice compositions which provide maximum antibacterial agent availability in brushing solutions formed using the dentifrice.

It is known to the art that water soluble alkali and alkaline metal salts, such as sodium, potassium, calcium salts when present in dentifrice formulations, inhibit the bioavailability of nonionic antibacterial agents such as Triclosan, so that when the dentifrice is applied to the teeth, the bioavailability of Triclosan is inhibited to a level whereby little antiplaque effect is achieved. This inhibitory effect is noted even when the calcium salt is substantially water insoluble as is the case with calcium abrasive agents such as dicalcium phosphate compounds which are widely used in dental formulations.

Thus, there is a clear need in the art to formulate a dentifrice product capable of delivering both a nonionic antibacterial agent and a calcium salt during tooth brushing whereby the ingredients used to prepare the dentifrice composition do not inhibit the bioavailability of the nonionic antibacterial agent present so that optimum uptake of the antibacterial agent occurs.

SUMMARY OF THE INVENTION

In accordance with the present invention there is provided a composition and method for applying a dentifrice composition containing both a nonionic antibacterial agent and a calcium salt, to the teeth, wherein the nonionic antibacterial agent and calcium salt are each incorporated in separate dentifrice components which are physically separated until dispensed for use, the first component being an aqueous composition containing the nonionic antibacterial agent and the second component being a composition containing a calcium salt normally incompatible with the nonionic antibacterial agent whereby maximum delivery of the agent is achieved upon mixing of the dentifrice components on application to the teeth.

DESCRIPTION OF THE PREFERRED EMBODIMENTS

The nonionic antibacterial agent used to prepare the first dentifrice component in accordance with the practice of the present invention is preferably a halogenated diphenyl ether compound. Halogenated diphenyl ether antibacterial compounds desirable from considerations of antiplaque effectiveness and safety include 2,4,4'-trichloro-2'-hydroxydiphenyl ether (Triclosan) and 2,2'-dihydroxy-5,5'-dibromodiphenyl ether. Other useful nonionic antibacterial agents include phenoic compounds including phenol and its homologs, mono and polyalkyl and aromatic halophenols, resorcinol and its derivatives and bisphenolic compounds, such phenolic compounds being more fully disclosed in U.S. Pat. No. 5,368,844, the disclosure of which is incorporated herein by reference. The nonionic antibacterial agent is incorporated in the first component of the dentifrice composition of the present invention at concentration of about 0.05 to about 3.0% by weight and preferably about 0.1 to about 1% by weight.

Examples of calcium salts useful in the practice of the present invention include water soluble salts such as calcium chloride, calcium acetate, calcium butylate, calcium citrate, calcium lactate, calcium salicylate as well as calcium salts of limited water solubility such as calcium carbonate, tricalciumphosphate, tetracalcium phosphate, calcium phosphate dihydrate, anhydrous dicalcium phosphate and calcium pyrophosphate.

The calcium salt is incorporated in the second component of the dentifrice composition of the present invention at a concentration of about 0.2% to about 5% by weight and preferably at about 1.0 to about 2.0% by weight when in the form of a water soluble salt and about 10 to about 60% by weight when present in an insoluble form as in the case of abrasives such as dicalcium phosphate.

The vehicle for the separate components of the dentifrice composition of the present invention is formulated, as further defined hereinunder, to form a semi-solid product of desired consistency which is extrudable from a pump or collapsible tube. In general, the liquids that form the vehicle will comprise water, in an amount ranging from about 10 to about 35% by weight and preferably about 10 to about 20% by weight and a humectant comprised of glycerin, sorbitol or a mixture of both in an amount ranging from 20 to about 40% by weight and preferably about 25 to about 35% by weight.

Thickeners such as natural and synthetic gums and colloids may also be incorporated in the dentifrice composition of the present invention. Examples of such thickeners include carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroyethyl cellulose. The thickener may be incorporated in the compositions of the present invention at a concentration of about 0.05 to about 2% by weight and preferably about 0.1 to about 1.5% by weight.

The nonionic antibacterial agent and calcium salt ingredients are contained in a vehicle formulated to have similar compositions so that two components will be of substantially equivalent rheologies, which will permit them to be synchronously coextrudable at a volume ratio of about 0.9:1 to about 1.0 to about 0.9 and preferably 1:1. In order that the physical characteristics of the second component have rheological properties substantially equivalent to the first component when the added calcium salt is an abrasive such as dicalcium phosphate, the vehicle composition of the second component, specifically the humectant and thickener content, is adjusted to accommodate the inclusion of the abrasive. As the calcium salt abrasive is included in the second dentifrice component at a concentration of about 10 to about 60% by weight, at these abrasive levels, the humectant concentration will range from about 15 to about 35% by weight and preferably about 20 to about 30% by weight. In such abrasive containing second component, as the inclusion of the abrasive has a thickening effect, a non-reactive abrasive such as silica may be included in the first component at a concentration of about 10 to about 25% by weight and preferably about 15 to about 20% by weight. Suitable silica compositions are available commercially as precipitated, amorphous silica, such as Zeodent 165 available from J. M. Huber Company as well as additional thickening agents such as amorphous silica at about 3 to about 10% by weight which are available from J. M. Huber Company under the trademark Zeodent 115.

A surfactant is used in the preparation of dentifrice components of the present invention to aid in the thorough dispersion of the dentifrice composition throughout the oral cavity when applied thereto as well as to improve the cosmetic acceptability and foaming properties of the dentifrice. Among the surfactants useful in the practice of the present invention are salts of the higher alkyl sulfates, such as sodium lauryl sulfate (SLS) or other suitable alkyl sulfate having 8 to 18 carbon atoms in the alkyl group; sodium lauryl sulfoacetate, salts of sulfonated monoglycerides of higher fatty acids, such as sodium coconut monoglycaride sulfoante or other suitable sulfoanted monoglycarides of a fatty acids of 10 to 18 carbon atoms; salts of amides of higher fatty acid, e.g., 12 to 16 carbon atom acids, with lower aliphatic amino acids, such as sodim-N-palmitoyl sarcosinates; salts of the esters of such fatty acids with isothionic acid or with glycerol monosulfate, such as the sodium salt of monosulfated monoglyceride of hydrogenated coconut oil fatty acids; salts ofolefin sulfoantes, e.g., alkene sulfonates or hydroxylakene sulfoantes or mixtures thereof having 12 to 16 carbon atoms in the carbon chain of the molecule; and soaps of higher fatty acids, such as those of 12 to 18 carbon atoms, e.g., coconut fatty acids. The cation of the salt may be sodium (which is preferred), potassium or mono- di or triethanol amine.

The surfactant is included in the dentifrice vehicle of the present invention at a concentration of about 0.5 to about 3.0% by weight and preferably about 1.0 to about 2.0% by weight.

An antibacterial enhancing agent may also be included in the oral composition. The use of antibacterial enhancing agents in combination with antibacterial agents such as Triclosan is known to the art, as for example, as disclosed in U.S. Pat. No. 5,188,821 and U.S. Pat. No. 5,192,531. Preferably, the antibacterial enhancing agent is an anionic polymeric polycarboxylate having a molecular weight of about 10,000 to about 1,000,000 preferably about 50,000 to about 800,000. Anionic polymeric polycarboxylates are generally employed in the form of their free acids or preferably as a partially or fully neutralized water soluble alkali metal salt, e.g., sodium, potassium or ammonium salts. Preferred antibacterial enhancing agents are 1:4 to 4:1 copolymers of maleic anhydride or acid with another polymerizable ethylenically unsaturated monomer, preferably a methyl vinyl ether/maleic anhydride copolymer having a molecular weight (M.W.) of about 30,000 to about 1,000,000, most preferably about 50,000 to about 800,000. These copolymers are available, for example, under the trademark Gantrez, e.g., Gantrez AN 139 (M.W. 500,000), AN 119 (M.W. 250,000); and preferably Gantrez S-97 Pharmaceutical Grade (700,000), of GAF Corporation. The antibacterial enhancing agent is incorporated in the compositions of the present invention in weight amounts of about 0.05 to about 5%, and preferably about 0.1 to about 4%.

Fluoride providing salts having anticaries efficacy may also be incorporated in the dentifrice components of the present invention and are characterized by their ability to release fluoride ions in water. It is preferable to employ a water soluble fluoride salt providing about 10–3,000 ppm of fluoride ion, and preferably about 1,000–2,000 ppm of fluoride ion. Among these materials are water soluble inorganic metal salts, for example, sodium fluoride, potassium fluoride, sodium monofluorophosphate and sodium fluorosilicate. Sodium fluoride and sodium monofluorophosphate are preferred fluoride providing salts. In the practice of the present invention the fluoride providing salts are incorporated in the nonionic antibacterial dentifrice component as these salts are incompatible with calcium salts forming insoluble calcium fluoride during storage of dentifrices in which both salts are present.

Salts having anticalculus efficacy including water soluble salts such as dialkali or tetraalkali metal pyrophosphate salts such as $Na_4P_2O_7$ (TSPP) $K_4P_2O_7$, $Na_2K_2P_2O_7$, $Na_2H_2P_2O_7$ and $K_2H_2P_2O_7$, long chain polyphosphate such as sodium hexametaphosphate and cyclic phosphates such as sodium trimetaphosphate as well as alkali metal tripolyphosphates such as sodium tripolyphosphate (STPP) and potassium tripolyphosphate may also be incorporated in the calcium salt containing dentifrice component of the present invention, preferably at a concentration of about 0.05 to about 8.0% by weight. In the practice of the present invention, antitartar pyrophosphate salts are incorporated in the calcium salt containing dentifrice component as the pyrophosphate salts inhibit the delivery to dental tissue of nonionic antibacterial agents such as Triclosan.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The pigments have a particle size in the range of 5–1000 microns, preferably 250–500 microns, and are present at a concentration of 0.5 to 3% by weight.

A striped dentifrice product is obtained in accordance with the practice of the present invention wherein colorants of contrasting colors are incorporated in each of the dentifrice components used in the practice of the present invention, the colorants being pharmacologically and physiologically nontoxic when used in the suggested amounts. Colorants used in the practice of the present invention include both pigments and dyes.

The dyes used in the practice of the present invention are distributed uniformly throughout the dentifrice component and are generally food color additives presently certified under the Food Drug & Cosmetic Act for use in food and ingested drugs, including dyes such as FD&C Red #3 (sodium salt of tetraiodofluorescein), FD&C Yellow #5 (sodium salt of 4-p-sulfophenylaxo-B-naphtol-6-monosulfonate), FD&C Green #3 (disodium salt of 4-{[4-(N-ethyl-p-sulfobenzylamino)-phenyl]-4-hydroxy-2-sulfoniumphenyl)-methylene}-[1-(N-ethyl-N-p-sulfobenzyl)-₂3,5-cyclohexadienimine], FD&C Blue #1 (disodium salt of dibenzyldiethyl-diaminotriphenylcarbinol trisulfonic acid anhydrite), FD&C Blue #2 (sodium salt of disulfonic acid of indigotin) and mixtures thereof in various proportions. The concentration of the dye for the most effective result in the present invention is present in the dentifrice composition in an amount from about 0.0005% to about 2% by weight.

It is preferred that the colorant included in one of the dentifrice components be a pigment such as $TiO_2$ and that the colorant distributed throughout the body of the other dentifrice component be a dye and that the dye be of a different color than the colorant included in the first dentifrice component.

Any suitable flavoring or sweetening material may also be incorporated in the dentifrice components of the present invention. Examples of suitable flavoring constituents are flavoring oils, e.g., oils of spearmint, peppermint, wintergreen, sassafras, clove, sage, eucalyptus, marjoram, cinnamon. Lemon, and orange, and methyl salicylate. Suitable sweetening agents include sucrose, lactose, maltose, sorbitol, xylitol, sodium cyclamate, perillartine, and sodium saccharin. Suitably, flavor and sweetening agents may together comprise from 0.01% to 5% by weight or more of the preparations.

The calcium salt containing dentifrice component of the present invention may be prepared by suitably mixing of the ingredients wherein the thickening agent is dispersed with humectants, sweetener and water. The calcium salt, surfactant tartar control agents such as TSPP, STPP with flavor and colorant are then separately added and uniformly dispersed. The dentifrice is then thoroughly deaerated (e.g., in vacuo) and packaged. The addition and mixing of the ingredients is conducted in a low humidity environment and preferably under a vacuum of 20–30 inches and preferably 28–30 inches mercury.

To prepare the antibacterial agent containing dentifrice component of the present invention, water, humectant, e.g., sorbitol, thickener and sweetener are dispersed in a conventional mixer until the mixture becomes a homogeneous gel phase. Into the gel phase are added a pigment such as $TiO_2$ and a fluoride anticaries agent such as sodium fluoride. These ingredients are mixed until a homogeneous phase is obtained. Thereafter the polishing agent, polymeric, polycarboxylate compound, antibacterial agent, flavor and surfactant ingredients are added and the ingredients mixed at high speed under vacuum of about 20–100 mm Hg. The resultant product is a homogeneous, semi-solid, extrudable paste product.

The dual component dentifrice composition of the present invention is packaged in a suitable dispensing container in which the components are maintained physically separated and from which the separated components may be dispensed synchronously. Such containers are known to the art. An example of such container is a dual compartmented dispensing container having collapsible sidewalls disclosed in U.S. Pat. No. 4,487,757 and 4,687,663 wherein the container body is formed from a collapsible plastic web and is provided with a partition within the container body defining separate compartment in which the physically separated components are stored and from which they are dispersed through a suitable dispensing outlet.

The following specific Example illustrates the present invention. The individual dentifrice components described below were prepared by following the procedure described above. The amounts of the various ingredients are by weight unless otherwise indicated. The resultant dentifrices were deaerated, packaged in tubes or other containers provided with means for physical separation of the individual dentifrice components.

EXAMPLE

A combined dentifrice component composition of the present invention, designated "Composition X", composed of a 1:1 volume mixture of dentifrice components A and B, hereinafter described, was prepared using the following ingredients:

| Ingredients | Dentifrice Component A | B | (% Total X Ingredients When Components A & B Combined at 1:1 volume ratio) |
|---|---|---|---|
| Deionized water | 13.3750 | 25.550 | 19.4625 |
| Sodium saccharin | 0.30 | 0.20 | 0.25 |
| Glycerin | 17.00 | 22.00 | 19.5 |
| Iota carrageenan | 0.7250 | 1.150 | 0.9375 |
| Dicalcium phosphate dihydrate | 0.00 | 48.760 | 24.38 |
| Flavor | 1.00 | 0.890 | 24.38 |
| Sodium lauryl sulfate | 1.500 | 1.200 | 0.945 |
| Tetrasodium pyrophosphate | 0.00 | 0.250 | 0.125 |
| Sodium fluoride | 0.4860 | — | 0.243 |
| Titanium dioxide | 0.500 | — | 0.25 |
| Sorbitol-non-crystallizing-(70% solution) | 14.504 | — | 7.252 |
| Gantrez S-97 | 27.200 | — | 13.6 |
| Sodium hydroxide (50% solution) | 2.160 | — | 1.08 |
| Zeodent 115 | 18.650 | — | 9.325 |
| Zeodent 165 | 2.00 | — | 1.0 |
| Triclosan | 0.600 | — | 0.3 |
| Total Materials | 100.00 | 100.00 | 100.00 |

The delivery of Triclosan from dentifrice components A and B when combined and mixed to form combined Composition X was determined using an in vitro test which measures the uptake and retention to tooth surfaces of Triclosan using disks of saliva coated hydroxyapatite (SCHAP), the mineral phase of dental enamel. This in vitro model for human teeth has been found, in clinical studies, to be correlatable to in vivo bioavailability of Triclosan on tooth surfaces.

In this in vitro test, hydroxyapatite disks (HAP), purchased from Clarkson Chromatography Products Inc., 213 Main Street, South Williamport, Pa. 17701, are hydrated with sterile water in a polyethylene test tube. The water is then removed and replaced with 2 milliliters (ml) of saliva. A salivary pellicle is formed by incubating the disk overnight at 37° C. with continuous shaking in a water bath. After this treatment, the saliva is removed and the disks are treated with 1.0 ml of a dentifrice slurry prepared by mixing the Triclosan containing dentifrice sample and water at 1:2 volume ratio and then centrifuged to separate the solid from the liquid phase. This 1:2 dentifrice water ratio approximates mouth conditions during tooth brushing. The liquid (supernatant) slurry is used to incubate the SCHAP disk at 37° C. with continuous shaking in a water bath. After 30 minutes, the disk is transferred into a new tube and 5 ml of water are added followed by shaking the disk gently with a Vortex. The disk is then transferred to a new tube and the washing procedure repeated twice. Finally, the disk is transferred to a new tube to avoid co-transfer of any liquid along with the disk. Then 1.0 ml of methanol is added to the disk and shaken vigorously with a Vortex. The sample is left at room temperature for 30 minutes to extract any absorbed Triclosan into the methanol. The methanol is then aspirated. After this treatment, the methanol is transferred into HPLC (high performance liquid chromatography) vials for determination of the concentration of Triclosan present. Triplicate samples are used in all tests.

The delivery and retention of Triclosan to SCHAP disks from the combined toothpaste components containing both Triclosan and calcium phosphate was determined by using the procedure described above. The uptake and retention of Triclosan from this dentifrice composition on the SCHAP disks is set forth in Table II below.

As a control, the above procedure was repeated, except no dicalcium phosphate was present in the toothpaste and was comparable to Triclosan containing toothpastes being presently sold commercially. This control toothpaste was designated "Composition Y" in Table II below. The uptake and retention of Triclosan from Composition Y on SCHAP disks is also set forth in Table II below.

TABLE II

| Composition | Triclosan Uptake µg/disk (± std. deviation) |
|---|---|
| X | 103.5 ± 0.5 |
| Y | 103.8 ± 0.9 |

The results recorded in Table II indicate that delivery of Triclosan to SCHAP disks is not impaired in any way by the presence of a calcium abrasive in a Triclosan containing dentifrice (Composition X) when the two ingredients are physically separated in separate dentifrice components during storage but dispensed together simultaneously.

The antiplaque activity of Composition X was assessed using a chemostat plaque model system of the type disclosed in the American Journal of Dentistry, Vol. 3, pages S8–S9 (1990). The chemostat consisted of a source of bacterial growth media contained in a mixing chamber and flow cells connected thereto. HAP disks of the type described above on which plaque was to be formed were fixed in the flow cells. A mixed culture of five species of oral microorganisms (*A. viscosus, S. mutans, S. sangius, V. parvula, F. nucleatum*) associated with human plaque was maintained in the chemostat, and the mixture was then pumped through flow cells at the rate of 1 ml/minute for 48 hours to grow plaque on the HAP disks.

To evaluate the antiplaque efficacy of the dentifrice combination, Composition X, the dentifrice was diluted 3:1 with water and pumped for 30 seconds at the rate of 6 ml/minute through the flow cells containing the HAP disks on which plaque was grown. Thereafter, bacterial plaque grown on the HAP disks was removed by immersion of the disks in 2 ml solution of 0.1N NaOH in a waterbath at 37° C. with gentle shaking for 15 minutes. The disks were removed from the NaOH solution and the solution was then sonically agitated to disperse the plaque. Turbidity Optical Density of the sonically agitated sample, a measure of plaque growth, was then determined by measuring the absorbance of 610 nm in a spectrophotometer. The Triclosan containing commercial type toothpaste Composition Y was used as a control. The results are recorded in Table III below.

TABLE III

| | Optical Density | |
|---|---|---|
| Composition | Run 1 | Run 2 |
| X | 0.2830 | 0.1385 |
| Y | 0.2668 | 0.1422 |

The results recorded in Table III show that the antiplaque activity of Composition X was not impaired as the optical density of the Composition X dentifrice solution was comparable to that of the control antibacterial toothpaste, Composition Y.

Composition X was evaluated for antibacterial efficacy in vitro against *A. viscosus* and *F. nucleatum,* two microorganisms present in human plaque, by the short interval killing test (SIKT) method. The SIKT test is an in vitro antimicrobial test which incorporates a fixed contact time wherein 1 ml of dentifrice diluted to 2 ml with water is mixed with a predetermined inoculum of *A. viscosus* ($10^6$–$10^7$) colony forming unit, (cfu/ml) for a 1–2 minute contact time. The system is then neutralized to inhibit further antibacterial activity. The surviving bacteria are enumerated using plate count methodology. The reduction in cfu counts compared to a water control is the basis for expressing antibacterial activity of the agents. The results of the SIKT test are recorded in Tables IV and V below.

TABLE IV

| | Bacterial Colonies (*A. viscosus*) | | |
|---|---|---|---|
| Composition | 1:100 dilution | 1:1000 dilution | 1:5000 dilution |
| X | 52 | 4 | 1 |
| Y | 39 | 7 | 1 |

TABLE V

| | Bacterial Colonies (*F. nucleatum*) | | |
|---|---|---|---|
| | 1:100 dilution | 1:1000 dilution | 1:5000 dilution |
| Composition Y | 163 | 62 | 5 |
| Composition X | 107 | 15 | 2 |

The results recorded in Tables IV and V confirm those of Table III, namely that the antibacterial activity of Triclosan is not impaired when the calcium abrasive and antibacterial agent remain separated until dispensed together simultaneously for application to the teeth by brushing.

What is claimed is:

1. A dual component dentifrice antiplaque composition in which a first component is a stable, extrudable dentifrice composition which is free of calcium ion and contains a nonionic antibacterial agent and the second component is an extrudable dentifrice composition in which a calcium containing salt is present, the first and second dentifrice components being synchronously extrudible when dispensed for application to the teeth, the first and second components being physically segregated prior to use, the components when mixed upon application to teeth providing maximum delivery of the nonionic antibacterial agent to dental tissue.

2. The composition of claim 1 wherein the calcium salt is dicalcium phosphate dihydrate.

3. The composition of claim 1 wherein the antibacterial agent is Triclosan.

4. The composition of claim 1 wherein a fluoride releasable salt is present in the first component.

5. The composition of claim 1 wherein an anticalculus pyrophosphate salt is present in the second component.

6. The composition of claim 5 wherein the pyrophosphate salt is an alkali metal pyrophosphate.

7. The composition of claim 1 wherein the components are extrudable at a volume ratio of about 0.9:1 to 1.0 to 0.9.

8. A method for the antibacterial treatment of teeth which comprises preparing a dual component dentifrice composition in which a first component is an extrudable dentifrice composition free of calcium ion and contains a nonionic antibacterial agent and a second component is an extrudible dentifrice composition containing a calcium salt, maintaining the first component physically separated from a second component, synchronously extruding the first and second components and then mixing the extruded components upon application to the teeth whereby maximum delivery of the antibacterial agent to the teeth is obtained.

9. The method of claim 8 wherein the calcium salt is dicalcium phosphate.

10. The method of claim 8 wherein the antibacterial agent is a halogenated diphenyl ether.

11. The method of claim 8 wherein the antibacterial agent is Triclosan.

12. The method of claim 8 wherein a fluoride salt is present in the first component.

13. The method of claim 8 wherein an antitartar pyrophosphate salt is present in the second component.

14. The method of claim 13 wherein the antitartar pyrophosphate salt is an alkali metal pyrophosphate.

15. The method of claim 11 wherein the components are extrudable at a volume ratio of about 0.9:1 to about 1:0.9.

16. The method of claim 11 wherein the components are extrudable at a volume ratio of about 1:1.

* * * * *